United States Patent [19]

Iinuma

[11] 4,186,747
[45] Feb. 5, 1980

[54] ULTRASONIC DIAGNOSING APPARATUS

[75] Inventor: Kazuhiro Iinuma, Yokohama, Japan

[73] Assignee: Tokyo Shibaura Electric Co., Ltd., Kawasaki, Japan

[21] Appl. No.: 820,148

[22] Filed: Jul. 29, 1977

[30] Foreign Application Priority Data

Jul. 30, 1976 [JP] Japan .................................. 51/90183

[51] Int. Cl.$^2$ ............................................ A61B 10/00
[52] U.S. Cl. ....................................... 128/660; 73/626
[58] Field of Search .................. 128/2 V, 2.05 Z, 660, 128/661; 73/625, 626, 633

[56] References Cited

U.S. PATENT DOCUMENTS

| 3,603,303 | 9/1971 | Stouffer | 128/2 V |
| 3,805,596 | 4/1974 | Klahr | 128/2.05 Z X |
| 3,881,466 | 5/1975 | Wilcox | 128/2 V |
| 3,927,661 | 12/1975 | Takemura | 128/2 V |
| 4,010,634 | 3/1977 | Baumgartner | 128/2 V X |
| 4,094,306 | 6/1978 | Kossoff | 128/2 V |

FOREIGN PATENT DOCUMENTS 3921580 10/1964 Japan .................................. 128/2 V

OTHER PUBLICATIONS

"Acoustic Holography . . . human body," Electronic Design, vol. 24, No. 13, pp. 38-39, Jun. 1976.
Griffith et al., "A Sector Scanner for Real Time . . . ," Circulation, vol. 49, Jun. 1974, pp. 1147-1152.
Kikuchi et al., "Early Cancer Diagnosis through Ultrasonics," J. Acoustical Soc. Am., vol. 29, No. 7, Jul. 1957, pp. 824-833.
Yoneda et al, "Ultrasonic Diagnostic Equipment for Mass Breast Survey," Jap. Article, Nov. 1975.

Primary Examiner—Lee S. Cohen
Attorney, Agent, or Firm—Finnegan, Henderson, Farabow & Garrett

[57] ABSTRACT

An ultrasonic diagnosing apparatus effects high speed ultrasonic scanning of a subject to be examined and produces and records a plurality of closely spaced, planar B-mode tomographic images. The diagnosing apparatus includes an ultrasonic probe having a linear array of ultrasonic converters, a mechanical apparatus to move the probe in a direction broadside to the linear array, an ultrasonic transmitting and receiving device for activating the electroacoustic converters and processing signals from the electroacoustic converters to form a plurality of closely spaced, planar B-mode tomographic images, a display device and a continuous recording device.

18 Claims, 5 Drawing Figures

ULTRASONIC DIAGNOSING APPARATUS

BACKGROUND OF THE INVENTION

This invention relates to an ultrasonic diagnosing apparatus.

An ultrasonic diagnosing apparatus is adapted to transmit ultrasonic beams toward a to-be-examined subject such as a living body from an ultrasonic probe, constituted of an array of electroacoustic converters, and receive the ultrasonic beams reflected from the region of interest of the living body to obtain living tissue data.

A general method for obtaining a tomographic image of the region of interest of a human being is by sequentially shifting ultrasonic beams from an electroacoustic converter array in a direction in which the electroacoustic converters are arranged, brightness-modulating electron beams in a CRT by an electric signal corresponding to the ultrasonic beam reflected from the region of the humam being and received by the electroacoustic converters, and making the sequential shift of the ultrasonic beams synchronous with a scanning line shift by the electron beams in CRT to display a tomographic image of the living body region on the CRT. Such a display mode is called a B-mode display and is disclosed in, for example, U.S. Pat. No. 3,881,466. A method for obtaining such sequentially shifted ultrasonic beams with electronic control is called as an electronic linear scan method and disclosed in, for example, U.S. Pat. No. 3,919,683. According to the B-mode method only one tomographic image is obtained which corresponds to one cross sectional region of the living body. Therefore, where any affected area of the human being is to be examined, it is necessary to beforehand locate any possible affected area of the human being by palpation, X-ray examination, etc. and examine its neighboring areas by observing a B-mode image obtained. Where the certified engineer performs such an operation, a plurality of B-mode images are obtained at an interval of, for example, 5 mm. Later, the doctor diagnoses an affected region of the living body on the basis of the B-mode images taken. With such a method, however, it is impossible to reduce the inter-cross-section spacing between adjacent B-mode images of the area of the living body to less than a certain extent. For this reason, it is difficult to obtain data for each significant inter-cross-section of the area of the living body. Furthermore, there is a fear that a living body may be jerked during examination and, in such a case, the inter-cross-section spacings of the area of the living body are often irregularly tomographed. Since the living body is moved to a considerable extent due to a heart beat and respiration, there is a great risk of erroneous diagonsis. For group diagnosis or mass-screening in particular, it is required that examination be completed in a brief period, and even in this case detailed data needs to be obtained.

In FIG. 1 is shown one of most recent ultrasonic diagnosing apparatus for "group diagnosis", as recently reported on an article of lecture, page 49—The 28th meeting of Japan Society of ultrasonics in medicine—in which an ultrasonic probe is moved in a direction vertical to the scanning surface of a living body. As will be evident from FIG. 1, a total of 26 seconds is required to scan 9 cross-section areas of the living body, since 2 seconds is taken for scanning one cross-section and 1 second is required for the probe to be moved to the next cross-section. During the scanning it is desirable, though difficult, that respiration be halted. A movement of 40 mm at maximum is effected to obtain 9 cross-sectional images and in this case the width at which the scanning is effected is narrow.

Japanese Patent Bulletin 21580/1964 discloses a method for obtaining a plane image on a plane which is a predetermined distance below the surface of a subject to be examined. In this method, however, it is impossible to obtain cross-sectional images of varying depth.

SUMMARY OF THE INVENTION

An object of this invention is to provide an ultrasonic diagnosing apparatus capable of providing a whole three-dimensional tomographic image corresponding to the region of interest of a subject to be examined and capable of providing sufficient data to a doctor so as to eliminate any risk of erroneous diagnosis.

According to one aspect of this invention there is provided an ultrasonic diagnosing apparatus adapted to transmit ultrasonic beams from an electroacoustic converter array so as to effect electronic scanning at high speed in a direction of the array, while moving the electroacoustic converter array in a direction perpendicular to the direction of the array, sequentially from tomographic images of the areas of a to-be-examined subject on the basis of electric signals obtained from the ultrasonic beams reflected from the subject, and produce the tomographic images, as required, while continuously storing the tomographic images, so that a whole tomographic image can be observed in a three-dimensional fashion.

DETAILED DESCRIPTION OF THE PREFERRED EMBODIMENTS

Figure 2:
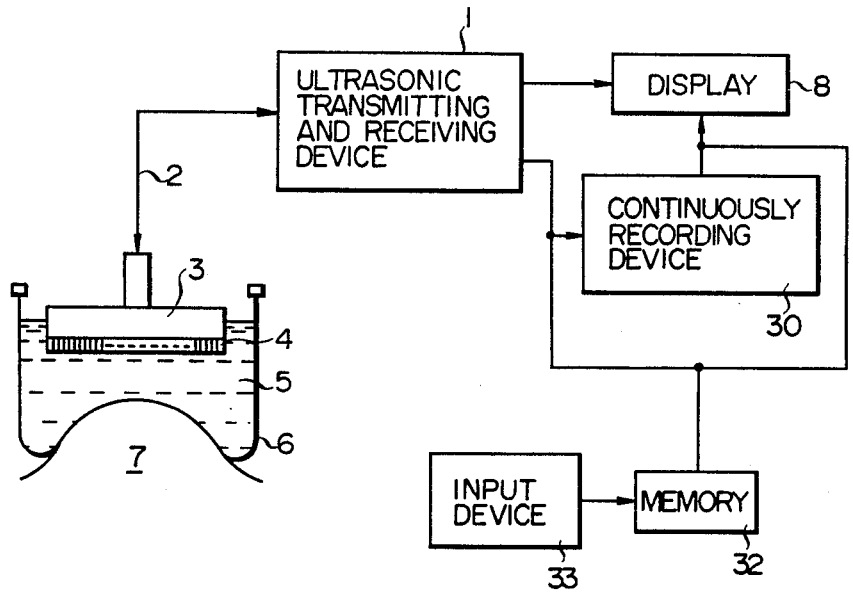
FIG. 2 is a block diagram showing an ultrasonic diagnosing apparatus according to one embodiment of this invention.
Figure 3:
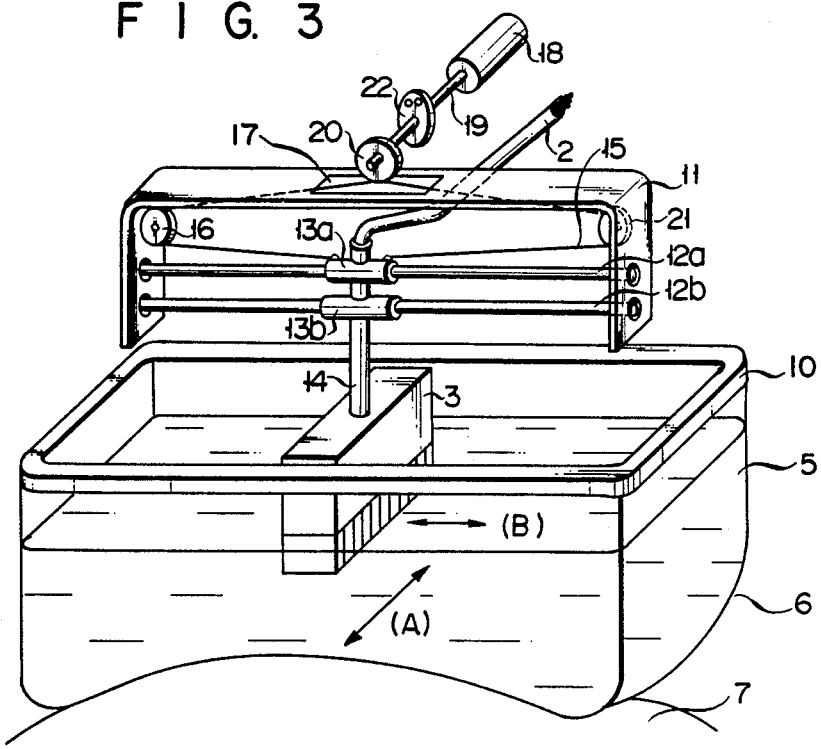
FIG. 3 is a perspective view showing a movement mechanism of an ultrasonic probe in the apparatus in FIG. 2.

In FIG. 2 an electric pulse delivered from an ultrasonic transmitting/receiving device is sent through a cable 2 to an array of electroacoustic converters 4 of an ultrasonic probe 3 to cause them to be driven to permit ultrasonic pulses to be emitted. The ultrasonic pulse is passed through a liquid 5, such as a degassed water, and through a bag 6, such as a very thin rubber sheet or a vinyl sheet, and directed into a subject to be diagnosed, such as a living body 7. The bag is held by support 10 (FIG. 3). The ultrasonic beam reflected on the living body 7 is received at the electroacoustic converters 4 where it is converted to a receiving signal. The receiving signal, after being processed at the ultrasonic transmitting/receiving device 1, is displayed as a tomographic image on a display unit 8. At this time, the first to eighth electroacoustic converters of the electroacoustic array 4 in FIG. 2 are driven by a first electric pulse which is sent from the ultrasonic transmitting-/receiving device 1. The ultrasonic transmitting/receiving device 1 is switched such that a receive/transmit operation is effected by a second electric pulse at the second to ninth electroacoustic converters of the electroacoustic array 4 as viewed from the left end of the electroacoustic array 4. In this way, the scanning of the living body 7 by the ultrasonic beam is effected with eight electroacoustic converters of the array 4 displayed one position to the right as one unit. Such a method is called as a linear scan method and is known, for example, in U.S. Pat. No. 3,919,683. Another method is also known in which pulses are supplied at mutually different times to a plurality of electroacoustic converters and the resultant ultrasonic beams are sectorially scanned, while deflected, with their wave fronts inclined to a varying degree. This method is called as a sector scan method. The method for effecting scanning by an ultrasonic beam under an electronic control is hereinafter referred to as a high-speed electronic scanning.

The ultrasonic probe 3 is continuously moved on the surface of the drawing sheet in the direction perpendicular to that of the array 4 while a high-speed electronic scanning is effected in the direction of the array 4. In FIG. 3 the ultrasonic probe 3 is mounted on the lower end of the support pipe 14 which is vertically fixed to collars 13a and 13b slidably fitted over parallel shafts 12a and 12b, respectively. The cable 2 is connected through the support pipe 14 to the converter 4. The collars 13a and 13b can be freely laterally moved with the shafts 12a and 12b as guides. A wire 15 is connected at one end to the end of the collar 13a. The wire 15 is taken out from a window 17 in a frame 11 through a pulley 16 mounted within the frame 11 and adapted to be run on a drive pulley 20 mounted on a drive shaft of a motor 18. The wire 15 is inserted through the frame window 17 into the interior of the frame 11, passed through a pulley 21 on the frame 11, and connected to the other end of the collar 13a. A potentiometer 22 is mounted on the drive shaft 19 of the motor 18 and the resistive value of the potentiometer 22 is varied according to the rotation of the shaft. In consequence, the lateral position of the ultrasonic probe 3 can be detected from the resistive value of the potentiometer 22.

For example, with 4KHz representing the repetition frequency of the ultrasonic pulse emitted, 10 cm the length of the probe 3 as measured in the direction A in FIG. 3, and 200 the number of scanning lines, a 20-frame-per-second image is obtained. In this case, the interval of the scanning lines corresponding to one frame of the image is 0.5 mm. If the probe 3 is moved a distance of 10 cm in 5 seconds at a constant speed in the direction of B in FIG. 4, 100 sheets of tomographic images of the living body 7 will be obtained in which the interval of 10 cm is divided into 1 mm spacings. Thus, data three-dimensionally representing the inner tissue of a living body having 10 cm×10 cm surface area can be obtained for a small time of 5 seconds. It is easy to stop respiration for about 5 seconds during examination. Even if the living body 7 is somewhat moved, the interval in which each cross-section of the living body 7 is scanned is 1/20 second and little problem arises even if the human being is jerked during examination.

Referring back to FIG. 2, the ultrasonic beams emitted from the ultrasonic probe 3 and reflected in the living body 7 are received at the ultrasonic probe 3 and, after being converted into electric pulses, are passed through the cable 2 to the ultrasonic transmitting-/receiving device 1 where they are processed. The processed pulses are connected to a display unit 8 where a tomographic image is displayed. The processed pulse is also supplied to a continuous recorder such as VTR. An image signal recorded on the continuous device 30 is sent, as required, to the display 8. It is also possible to display on the display unit 8 and to record in the recording device 30 data of date, patient's number and diagnosis from the input device 33. Such a continuous recorder 30 may be for example, a VTR on which an electric signal from the transmitting/receiving device 1 is directly recorded. Another method may be used in which an image projected onto the display unit is converted by, for example, an industrial TV camera and recorded in the VTR. A method for photographing an image displayed, for example, on the display unit 8 may be jointly used to obtain a fixed tomographic image.

The following description is given, by way of example, of the application of the ultrasonic diagnosing apparatus to a "group diagnosis" for breast cancer. In FIG. 3, reference numeral 7 is one breast of a human being, and a water bag 6 is placed on the breast of the human being. The water bag 6 is held by a frame 10 made of, for example, iron. The probe 3 is moved from left to right in the B direction while a high-speed electronic scanning is carried out in the A direction. As a result, the corresponding tomographic images are sequentially displayed onto the display unit 8 and the same images are placed in storage in the VTR 30. When the ultrasonic probe 3 is moved from left end to right end of the shafts 12a and 12b or from the left end to the right end of the shafts and back to be left end, one recording is completed. Before and after such recording, the name of the examinee, the date of examination, the to-be-examined area of examinee, etc. may be written onto the memory 32 from the input device 33. In this way, the examinees are one by one examined, and when the doctor can examine the region of interest at the time that the examination is given, he can evaluate the image on the display unit 8. If he is absent, a diagnosis is effected based on an image reproduced onto the display unit 8 from VTR 30.

Figure 4:
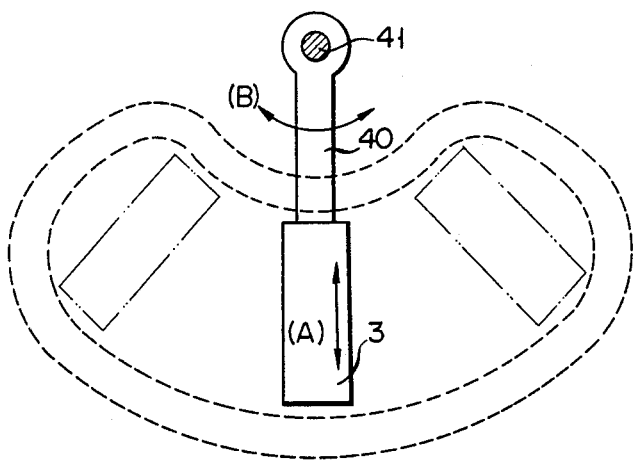
FIG. 4 is a diagram showing another example of the movement mechanism.
Figure 5:
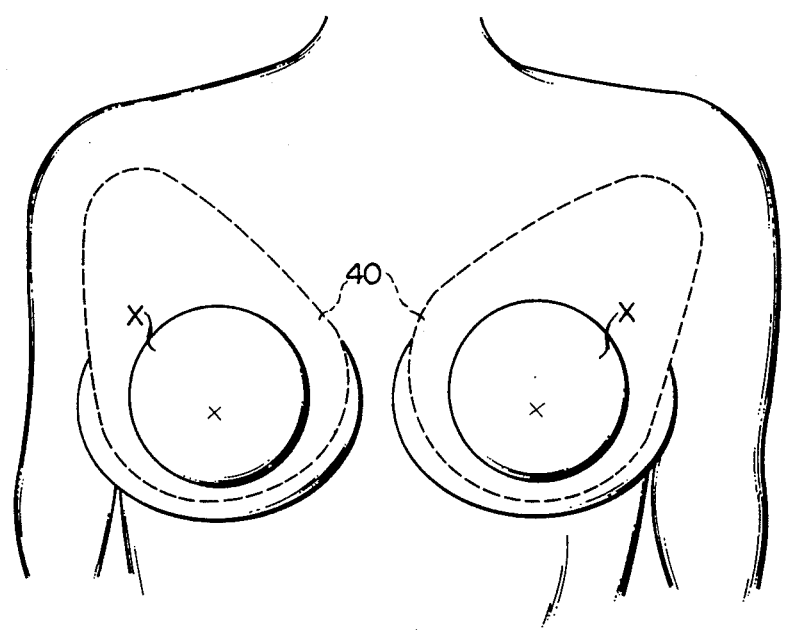
FIG. 5 is a plan view of the breast showing a place in which breast cancer is usually found.

The apparatus according to this invention can obtain a whole three-dimensional data of the examinee in a brief period and reproduce images on the display unit, as required, since a continuous recording is simultaneously made. The apparatus is very advantageous when it is used for "group diagnosis". For example, 2 minutes will be sufficient for an examinee to change clothes, and it is possible to examine more than 90 persons, for example, for 3 hours. The real time taken for obtaining tomographic image data is only 5 to 20 seconds per person. For group diagnosis the doctor normally give his evaluation based on the image data which have collectively been taken beforehand. Since only the recorded image data are relied upon, even if 20 seconds are taken per person, 30 minutes will be sufficient to diagnose 90 persons. This prominently alleviates the doctor's burden by diminishing the time required to diagnose one person. Furthermore, since the "region of interest" of the examinee is scanned at a very narrow width, a whole three-dimensional data is recorded irrespective of the degree of skill of the engineer, and in consequence there is no risk of an erroneous diagnosis or overlooking. For VTR, by using a magnetic sheet frame memory which records static images of the region of interest from the VTR, a necessary image can be examined without haste. It is also possible to take its photograph. The examinees can be classified into a positive, psuedo-positive, and negative type. A detailed examination can again be made for persons found to be positive or pseudo-positive. The occurence of breast cancer is usually developed in the areas indicated by dotted lines in FIG. 5, and in order to cover such an area a method as shown in FIG. 4 may be adopted. In FIG. 4 a support rod 40 is mounted on the side of the probe 3 and is rotated with an axis 41 as a center. The direction A, B of FIG. 3 corresponds to the direction A, B of FIG. 4, respectively.

When a normal video-tape recorder (VTR) is used as a continuous recorder, data corresponding to 90 persons can be adequately recorded onto one cassette VTR tape, providing that 20 seconds is taken per person. As a result, the apparatus of this invention provides a very increased amount of data per person and a great saving in cost in comparison with a conventional record by photographing.

If as a liquid 5 in the bag 6 in FIGS. 2 and 3 use is made of, in addtion to a degassed water, sodium chloride solution or oil with an acoustic impedance near to that of the surface of the living body and a temperature of approximately 37° C., the outline of the surface of the living body hardly appears on the image, making it possible to clarify the contour of the surface of the living body. The acoustic impedance of the liquid 5 can be selected to have a proper value dependent upon the subject to be diagnosed.

In the embodiment shown in FIGS. 2 and 3 the water bag is placed on the living body. Instead, a bag or container may be contacted with the living body through a hole provided in the bed, i.e. contacted from under. In this case, the probe is moved in a liquid of the container.

Figure 1:
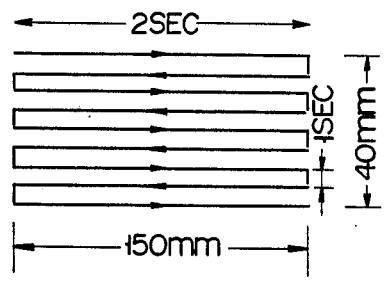
FIG. 1 is a line diagram showing the state in which a conventional ultrasonic probe is moved in the lateral and longitudinal directions.

Although in FIG. 1 the ultrasonic probe 3 is connected through the cable 2 to the ultrasonic transmitting and receiving device 1, part of the ultrasonic transmitting and receiving device 1 may be built in the ultrasonic probe 3.

What is claimed is:

1. An ultrasonic diagnosing apparatus for examining a subject comprising:
   an ultrasonic probe having a linear array of closely spaced electroacoustic converters for transmitting a plurality of ultrasonic beams to the subject, sensing the ultrasonic beams reflected from the subject and converting the received ultrasonic beams to electric, tomographic signals,
   means for electronically activating the electroacoustic converters to effect repeatedly a plurality of sequential, high-speed electronic, ultrasonic scans along the direction of the linear array,
   means for continuously moving the ultrasonic probe in a direction substantially broadside to the linear array during the period that the activating means effects said scans,
   means for processing the electric, tomographic signals from the electroacoustic converters to form sequentially from the electric, tomorahic signals representing each scan a respective planar, B-mode tomographic image in a plane parallel to the beams transmitted by the array of electroacoustic converters, and
   means for recording the plurality of planar B-mode tomographic images as they are formed by said processing means to obtain a three-dimensional representation of the subject.

2. An ultrasonic diagnosing apparatus according to claim 1, wherein said recording means includes a video tape recorder and an input device connected to the recorder for inputting to the video tape recorder data in addition to the planar, B-mode tomographic images.

3. An ultrasonic diagnosing apparatus according to claim 1, wherein said moving means comprises a support fixedly connected to the ultrasonic probe, a guide mechanism slidably holding the support with the array of electroacoustic converters being held substantially perpendicular to the guide mechanism, a wire with both its ends connected to the support, and a drive mechanism means for sliding the support along the guide mechanism by driving the wire along the guide mechanism.

4. An ultrasonic diagnosing apparatus according to claim 3, wherein said drive mechanism means includes a motor and a drive pulley mounted on the rotation shaft of the motor and around which the wire is run, and wherein said moving means further includes a potentiometer mounted on the shaft of the motor to detect the position of the probe by the rotation position of the motor shaft.

5. The ultrasonic diagnosing apparatus of claim 1 further comprising means for selectively reading the recorded tomographic images out of the recording means and displaying those tomographic images.

6. The ultrasonic diagnosing apparatus of claim 1 wherein said electroacoustic converters are spaced not greater the 1 mm apart.

7. The ultrasonic diagnosing apparatus of claim 1 wherein said activating means effects at least ten scans per second.

8. The ultrasonic diagnosing apparatus of claim 1 further comprising means for simultaneously displaying the planar, B-mode tomographic images as they are formed by said processing means.

9. The diagnosing apparatus of claim 1 wherein said moving means moves the ultrasonic probe at a constant speed.

10. An ultrasonic diagnosing apparatus for examining a subject comprising:
    an ultrasonic probe having a linear array of closely spaced electroacoustic converters for transmitting a plurality of ultrasonic beams to the subject, sensing the ultrasonic beams reflected from the subject and converting the received ultrasonic beams to electric, tomographic signals,
    means for electronically activating the electroacoustic converters to effect repeatedly a plurality of sequential, high-speed electronic, ultrasonic scans along the direction of the linear array,
    a support supporting the ultrasonic probe rotatably about an axis on the line defined by the array of electroacoustic converters,
    means for continuously rotating the probe about the support in a direction substantially broadside to the linear array during the period that the activating means effects said scans,
    means for processing the electric, tomographic signals from the electroacoustic converters to form sequentially from the electric, tomographic signals representing each scan a respective planar, B-mode tomograpahic image in a plane parallel to the beams transmitted by the array of electroacoustic converters, and means for recording the plurality of planar, B-mode tomographic images as they are formed by said processing means to obtain a three-dimensional representation of the subject.

11. The ultrasonic diagnosing apparatus of claim 10 further comprising means for selectively reading the recorded tomographic images out of the recording means and displaying those tomographic images.

12. An ultrasonic diagnosing appartus for examining a subject comprising:
an ultrasonic probe having a linear array of electroacoustic converters spaced not greater than 1 mm apart for transmitting a plurality of ultrasonic beams to the subject, sensing the ultrasonic beams refected from the subject and converting the received ultrasonic beams to electric, tomographic signals,
means for electronically activating the electroacoustic converters to effect repeatedly a plurality of sequential, high-speed electronic, ultrasonic scans along the direction of the linear array, said means effecting at least ten high-speed electronic, ultrasonic scans per second,
means for continuously moving the ultrasonic probe in a direction substantially broadside to the linear array during the period that the activating means effects said scans,
means for processing the electric, tomographic signals from the electroacoustic converters to form sequentially from the electric, tomographic signals representing each scan a respective planar, B-mode tomographic image in a plane parallel to the beams transmitted by the array of electroacoustic converters, and
means for recording a plurality of tomographic images as they are formed by said processing means to obtain a three-dimensional presentation of the subject.

13. The ultrasonic diagnosing apparatus of claim 12 further comprising means for selectively reading the recorded tomographic images out of the recording means and displaying those tomographic images.

14. The diagnosing apparatus of claim 12 further comprising means for simultaneously displaying the planar, B-mode tomographic images as they are formed by said processing means.

15. The diagnosing apparatus of claim 12 wherein the probe is 10 cm long and the moving means moves the probe a distance of 10 cm in one direction at a constant rate.

16. The ultrasonic diagnosing apparatus of claim 12 wherein the probe includes at least 200 electroacoustic converters to produce at least 200 scanning beams.

17. The ultrasonic diagnosing apparatus of claim 12 wherein the electronically activating means activates the electroacoustic converters at a frequency of at least 4 KHz and the processing means produces at least 20 frames of planar, B-mode images per second.

18. The diagnosing apparatus of claim 12 wherein the recording means includes a video tape recorder and an input device connected to the recorder for inputting to the video tape recorder data in addition to the tomographic images.

* * * * *